(12) United States Patent
Kinoshiro et al.

(10) Patent No.: US 8,865,471 B2
(45) Date of Patent: Oct. 21, 2014

(54) METHOD FOR ANALYZING METAL MATERIAL

(75) Inventors: Satoshi Kinoshiro, Tokyo (JP); Tomoharu Ishida, Tokyo (JP)

(73) Assignee: JFE Steel Corporation (JP)

(*) Notice: Subject to any disclaimer, the term of this patent is extended or adjusted under 35 U.S.C. 154(b) by 280 days.

(21) Appl. No.: 13/131,327

(22) PCT Filed: Dec. 25, 2008

(86) PCT No.: PCT/JP2008/073934
§ 371 (c)(1),
(2), (4) Date: Jun. 8, 2011

(87) PCT Pub. No.: WO2010/061487
PCT Pub. Date: Jun. 3, 2010

(65) Prior Publication Data
US 2011/0240477 A1 Oct. 6, 2011

(30) Foreign Application Priority Data
Nov. 28, 2008 (JP) .................. 2008-303356

(51) Int. Cl.
*G01N 33/20* (2006.01)
*G01N 31/02* (2006.01)

(52) U.S. Cl.
CPC .............. *G01N 31/02* (2013.01); *G01N 33/20* (2013.01)
USPC ................ 436/78; 436/73; 436/83; 205/790; 205/790.5

(58) Field of Classification Search
CPC .................. G01N 33/20; G01N 31/22
See application file for complete search history.

(56) References Cited

U.S. PATENT DOCUMENTS
5,985,674 A 11/1999 Umezawa et al.

FOREIGN PATENT DOCUMENTS
JP 05-346387 A 12/1993
JP 10-026618 A 1/1998
JP 2004-317203 A 11/2004

OTHER PUBLICATIONS

Rivas et al. "Electrochemical extraction of microalloy carbides in Nb-steel" Revista de Metallurgia, 2008, v. 44, No. 5, pp. 447-456.*
"Iron and Steel Manual 4th," *The Iron and Steel Institute of Japan*, Jul. 2002, vol. 4, part 2, 3.5, cover and 24 pages.
Inose, M. et al., "The Development of Determination Technique with High Precision for Precipitates Existing in the Surface of the Steel," *Materials and Processes*, 2005, vol. 18, No. 3, p. 660 (2 sheets).
Inose, M. et al., "Depth Profile Analysis of Precipitates and Inclusions Existing in the Surface of the Steel by Inductively Coupled Plasma Mass Spectrometry with Microwave Decomposition," *Bunseki Kagaku*, 2007, vol. 56, No. 2, pp. 93-98 in Japanese and 1 page summary in English.

* cited by examiner

*Primary Examiner* — Yelena G Gakh
(74) *Attorney, Agent, or Firm* — DLA Piper LLP (US)

(57) ABSTRACT

A method for analyzing a metal material includes electrolyzing a metal sample in an electrolytic solution, immersing a remaining portion of the metal sample taken out of the electrolytic solution in a dispersible solution to separate at least one substance selected from the group consisting of precipitates and inclusions attached to the remaining portion of the metal sample, filtering the dispersible solution containing the at least one separated substance through filters having straight pores and a porosity of 4% or more to obtain residues trapped on the filters and filtrates, and analyzing at least one of the residues and the filtrates.

8 Claims, 9 Drawing Sheets

METHOD FOR ANALYZING METAL MATERIAL

RELATED APPLICATIONS

This is a §371 of International Application No. PCT/JP2008/073934, with an international filing date of Dec. 25, 2008 (WO 2010/061487 A1, published Jun. 3, 2010), which is based on Japanese Patent Application No. 2008-303356, filed Nov. 28, 2008, the subject matter of which is incorporated by reference.

TECHNICAL FIELD

This disclosure relates to methods for analyzing precipitates and/or inclusions (hereinafter referred to as "precipitates and the like") in metal materials and particularly relates to a method for accurately and quantitatively analyzing nanometer-sized fine precipitates and the like by size.

BACKGROUND

Precipitates and the like in metal materials have significant influences on, for example, material properties such as mechanical properties and electromagnetic properties depending on the morphology, size, and distribution thereof. In recent years, as techniques for enhancing steel properties using precipitates and the like have been greatly developed particularly in the field of iron and steel, the control of such precipitates and the like in manufacturing steps has become important.

In general, precipitates and the like contained in steel materials are grouped into those which increase properties, those which reduce properties, and those which do not contribute to properties. It is important to stably form precipitates and the like having a certain size and composition to produce steel materials with desired properties. In, for example, precipitation-hardened high-tensile strength steel sheets, attempts have been made to form fine precipitates and the like to allow the steel sheets to have increased tensile strength and nanometer- to sub-micrometer-sized extremely fine precipitates and the like are recently controlled. Therefore, there are strong demands for methods capable of quantitatively analyzing elements contained in nanometer- to sub-micrometer-sized precipitates by size.

The Iron and Steel Institute of Japan, "Handbook of Iron and Steel 4th edition (CD-RM)," Vol. 4, Section 2, 3.5 discloses techniques such as acidolysis, halolysis, and electrolysis, for quantifying precipitates and the like in steel materials. The Iron and Steel Institute of Japan, "Handbook of Iron and Steel 4th edition (CD-RM)," Vol. 4, Section 2, 3.5 describes that an electrolytic method performed in accordance with a procedure shown in FIG. 1 is particularly excellent. In the electrolytic method, an iron matrix is dissolved in an electrolytic solution and a filter is used as a solid-liquid separator for collecting precipitates and the like dispersed in the electrolytic solution. All the precipitates and the like are collected by the combination of the aggregation of relatively small precipitates and the like with the clogging of pores of the filter by relatively large precipitates and the like. That is, the aggregated relatively small precipitates and the like are deposited on the filter because of the clogging of the filter pores by the relatively large precipitates and the like and the precipitates and the like deposited on the filter fulfill a cake filtration function (a filtration mechanism in which the deposited precipitates and the like serve as a filter), whereby all the precipitates and the like are collected. Therefore, the whole of the precipitates and the like can be analyzed. However, no information on the size of the precipitates and the like can be obtained.

Several techniques for quantifying precipitates and the like by size have been proposed on the basis of the techniques disclosed in The Iron and Steel Institute of Japan, "Handbook of Iron and Steel 4th edition (CD-RM)," Vol. 4, Section 2, 3.5. However, these techniques are central to breaking the aggregation of precipitates and the like and/or preventing the formation of cake layers (sedimentary layers of precipitates and the like on filters). For example, Japanese Examined Patent Application Publication No. 53-37595 discloses a technique in which non-metallic inclusions in steel materials are chemically separated in a liquid, ultrasonic waves are effectively applied to the liquid during filtration using a metal filter such that the aggregation of the non-metallic inclusions is broken and the formation of cake layers is prevented, and the non-metallic inclusions are thereby fractionated by size. However, it is problematic to apply the technique disclosed in JP '595 to aggregates of nanometer- to sub-micrometer-sized extremely fine precipitates and the like although the technique is effective for coarse non-metallic inclusions of several micrometers or more. This is because since more fine particles exhibit stronger aggregation in liquids, it is difficult to break the aggregates of the nanometer- to sub-micrometer-sized extremely fine precipitates by applying ultrasonic waves to the aggregates and there is no metal filter having nanometer- to sub-micrometer-sized filter pores sufficient to exert the effect of ultrasonic waves. Japanese Unexamined Patent Application Publication No. 58-119383 discloses a technique in which precipitates and the like with a size of 1 μm or less are fractionated by ultrasonic vibration using an organic filter with a filter pore size of 1 μm or less. However, it is difficult for the technique disclosed in Japanese Unexamined Patent Application Publication No. 58-119383, as well as that disclosed in JP '595, to break aggregates of such fine precipitates and the like with a size of 1 μm or less by ultrasonic vibration. Unlike metal filters, organic filters insufficiently propagate or reflect ultrasonic waves because of material properties. Therefore, filter pores cannot be unclogged by ultrasonic vibration and cake layers are formed on the filters. Hence, precipitates cannot be fractionated in accordance with the filter pore size. The Japan Institute of Metals, "Materia Japan," Vol. 45, No. 1, p. 52 (2006) discloses a technique in which precipitates and the like in a copper alloy are fractionated by size such that filtration is performed twice using filters having different filter pore sizes. However, the technique disclosed in The Japan Institute of Metals, "Materia Japan," Vol. 45, No. 1, p. 52 (2006) is not effective in solving problems associated with the aggregation of precipitates and the like or the formation of cake layers. Hence, analysis by size cannot be accurately performed.

Conventional techniques have problems with the aggregation of precipitates and the like and formation of cake layers as described above and, therefore, are not capable of accurately and quantitatively analyzing nanometer- to sub-micrometer-sized precipitates and the like (particularly precipitates and the like with a size of 1 μm or less and more preferably 200 nm or less) by size.

It could therefore be helpful to provide a method for accurately and quantitatively analyzing nanometer-sized fine precipitates and the like contained in a metal material by fractionating the precipitates and the like by size.

SUMMARY

We provide a method for analyzing a metal material, including electrolyzing a metal sample in an electrolytic solution, immersing a remaining portion of the metal sample taken out of the electrolytic solution in a dispersible solution to separate at least one substance selected from the group consisting of precipitates and inclusions attached to a remaining portion of the metal sample, filtering the dispersible solution containing the at least one separated substance through filters having straight pores and a porosity of 4% or more to obtain residues trapped on the filters and filtrates, the straight pores being filter pores which have a certain aperture shape and which extend through surfaces of the filters, and analyzing at least one of the residues and the filtrates.

BRIEF DESCRIPTION OF THE DRAWINGS

FIG. 3 is a schematic view of an example of an electrolyzer used in a method for analyzing precipitates and the like.

FIG. 4 is an illustration showing an example of an operational flow of an analytical method for analyzing precipitates and the like.

FIG. 6 is a graph showing the relationship between the absolute value of the zeta potential and the content of titanium in precipitates and the like.

Figure 1:
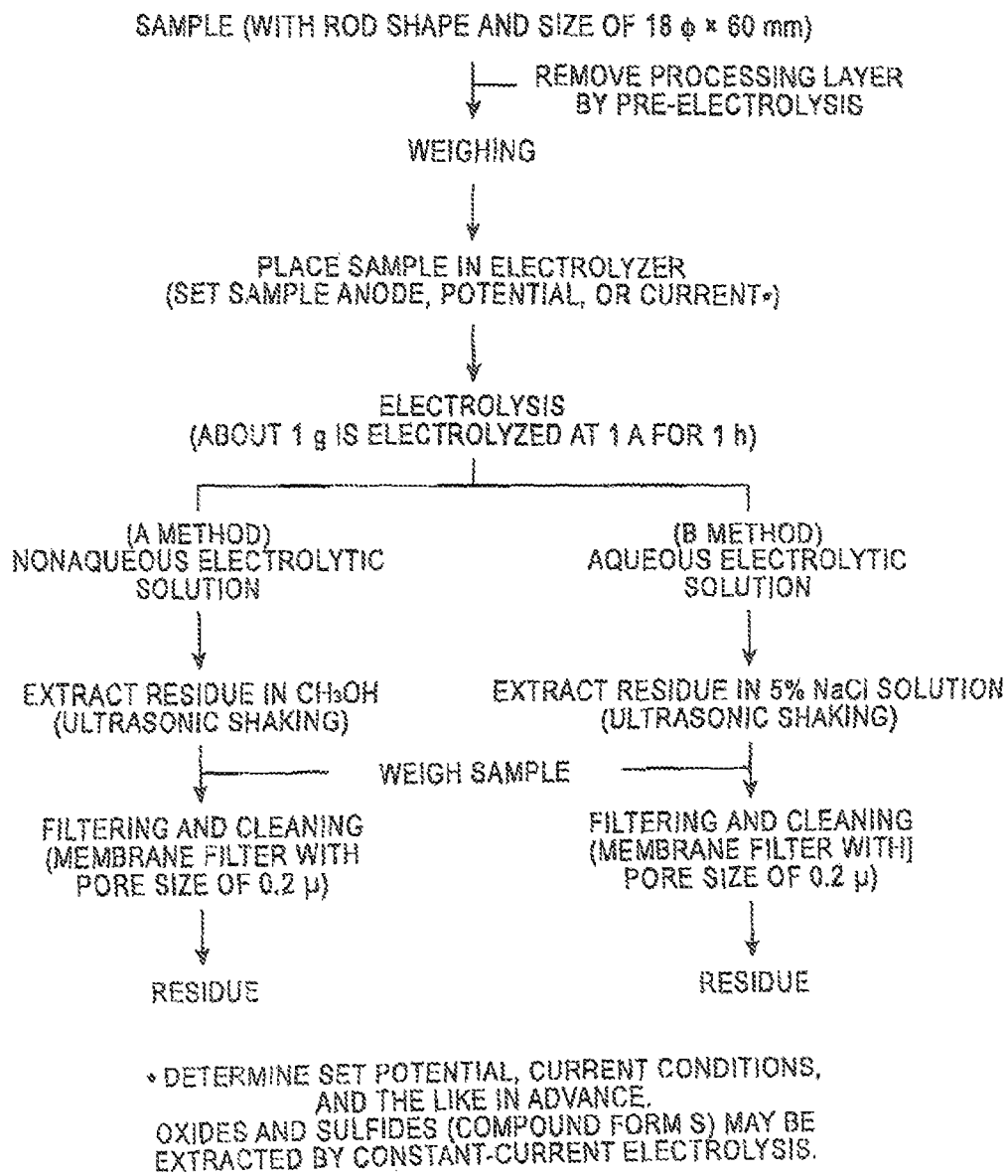
FIG. 1 is an illustration showing an operational flow of an electrolytic process described in The Iron and Steel Institute of Japan, "Handbook of Iron and Steel 4th edition (CD-RM)," Vol. 4, Section 2, 3.5.

Reference numerals in the drawings are as described below:
1 sample
2, 2a fixture
3 electrode
4 beaker
5 constant-current power supply
6 electrolytic solution
7 electrolyzer

DETAILED DESCRIPTION

An electrolytic extraction method disclosed in The Iron and Steel Institute of Japan, "Handbook of Iron and Steel 4th edition (CD-Rm)," Vol. 4, Section 2, 3.5 is capable of stably collecting precipitates and the like in steel by dissolving an iron matrix as shown in FIG. 1 and is regarded as a normal method (hereinafter referred to as a "standard method") for collecting and analyzing precipitates and the like. JP '595 and JP '383 described above are based on the standard method. However, the standard method and the conventional methods have various problems as described above.

Problems that we found with the standard method are as summarized below:
  Methanol is used as a dispersion medium for separated precipitates and the like although methanol has low ability to disperse precipitates and the like.
  A filter suitable for total collection is used although the filter is likely to be clogged.

The above problems probably prevent fine precipitates and the like from being fractionated by size. That is, since methanol, which has low ability to disperse precipitates and the like, is used as a dispersion medium, the fine precipitates and the like are readily aggregated. Hence, aggregates thereof cannot be completely broken even if a physical action such as an ultrasonic wave is applied thereto. Furthermore, use of the filter likely to be clogged allows the aggregated precipitates and the like to clog filter pores and therefore a cake layer is likely to be formed. As a result, it is probably difficult to fractionate nanometer- to sub-micrometer-sized precipitates and the like by size.

Therefore, we investigated dispersion media for precipitates and the like to prevent the aggregation of the precipitates and the like and found that dispersibility can be imparted to precipitates and the like with a size of 1 μm or less by the electrochemical action of an aqueous dispersion medium (hereinafter referred to as a "dispersible solution").

However, a major component of the electrolytic solution used in the standard method is methanol, which is low in dispersibility. Hence, to impart dispersibility to precipitates and the like, the precipitates and the like need to be transferred from the electrolytic solution to a dispersible solution. Therefore, a solid-liquid separation operation is necessary to separate the precipitates and the like from the electrolytic solution. We performed a "filtration" operation, which is a solid-liquid separation means, to collect the precipitates and the like in the electrolytic solution and the precipitates and the like in a dispersion medium (in particular, methanol) in accordance with a conventional standard method and found that some of the precipitates and the like (in particular, nanometer- to sub-micrometer-sized fine ones having a size of 200 nm or less) may possibly be lost.

On the basis of this result, we used steel samples to achieve solid-liquid separation means other than the conventional standard method. As a result, we found that almost all precipitates and the like are attached to the steel samples during and/or after electrolysis. This is a completely new finding. This finding suggests that solid-liquid separation can be readily achieved such that a remaining portion of a steel sample is taken out of an electrolytic solution during and/or after electrolysis. Furthermore, aggregation of the precipitates and the like can be prevented such that the precipitates and the like are separated in a dispersible solution in combination with the finding for solving the problem with aggregation. This attachment phenomenon is not entirely clear and is probably due to the electrical interaction between the steel sample and the precipitates and the like during and/or after electrolysis.

Thus, aggregation of the precipitates and the like can be prevented such that the precipitates and the like, which are attached to the steel sample, are highly dispersed in the dispersible solution by an electrical action. As a result, it is not necessary that a physical action such as an ultrasonic wave is applied to a solvent (including water and methanol) during filtration as disclosed in JP '595 and JP '383. This allows the following filters to be used: filters which are weak in material or structure and which are prevented from being used because of the use of ultrasonic waves and filters which are soluble in non-aqueous solvents and which are prevented from being used because of the use of methanol.

The scope of this disclosure is not limited to the case where only precipitates and the like attached to a remaining portion of a metal sample are analyzed. That is, results obtained by analyzing precipitates and the like that are contained in an electrolytic solution for some reason can be added to those obtained from the precipitates and the like attached to the remaining portion of the metal sample. This may provide more accurate analysis data in some cases.

Furthermore, we investigated filters for the purpose of preventing formation of cake layers and found that the shape of pores of filters and the porosity thereof relate closely to the formation of cake layers.

In the case of fractionating precipitates and the like by size, it is advantageous to use a filter which has filter pores allowing the precipitates and the like to pass therethrough and which is high in porosity. However, the precipitates and the like cannot be accurately fractionated only by the use of the filter, which is high in porosity, because precipitates and the like having a size not less than the pore size of the filter are trapped by the filter.

Therefore, we found that the filter pores need to have filter pores which have a certain aperture shape and which extend through a surface of the filter. Filter pores which have a certain aperture shape and extend through filter surfaces hereinafter referred to as "straight pores." Filter pores other than the straight pores have a function of depth filtration (a filtration mechanism in which particles are not trapped on filter surfaces, but are trapped in filter pores) or have a wide distribution of pore sizes. Hence, fine precipitates and the like that should essentially pass through filters are probably trapped by the filters.

Thus, the use of a high-porosity filter having straight pores is effective in fractionating nanometer- to sub-micrometer-sized precipitates and the like. Common examples of the high-porosity filter, which has such straight pores, include filters made of glass or ceramic. These filters are structurally weak because of the porosity thereof and therefore have not been used for ultrasonic filtration. We achieved this finding in combination with a method for dispersing precipitates and the like. Filters made of metal or the like can be used herein if the filters meet the above requirements. However, filters having nanometer- to sub-micrometer sized pores have not been commercially available.

We provide a method, including the following steps, for analyzing a metal material:
- an electrolysis step of electrolyzing a metal sample in an electrolytic solution;
- an immersion step of immersing a remaining portion of the metal sample taken out of the electrolytic solution in a dispersible solution for the purpose of separating at least one substance selected from the group consisting of precipitates and inclusions attached to the remaining portion of the metal sample;
- a fractionation step of filtering the dispersible solution containing the at least one separated substance through filters having straight pores and a porosity of 4% or more to obtain residues trapped on the filters and filtrates, the straight pores being filter pores which have a certain aperture shape and which extend through surfaces of the filters; and
- an analysis step of analyzing at least one of the residues and the filtrates.

The fractionation step is preferably that the filters have different filter pore sizes and are used to filter the dispersible solution in decreasing order of filter pore size such that the residues trapped on the filters and the filtrates are obtained. The filters preferably have a pore size of 10 nm to 500 nm and more preferably 20 nm to 200 nm.

The fractionation step preferably includes fractionating at least one substance selected from the group consisting of precipitates and inclusions having a size less than 1 µm.

The metal sample-analyzing method preferably further includes a step of analyzing at least one substance selected from the group consisting of the precipitates and inclusions attached to the remaining portion of the metal sample.

The dispersible solution preferably has a zeta potential with an absolute value of 30 mV or more with respect to at least one selected from the group consisting of the precipitates and inclusions to be analyzed.

The dispersible solution preferably contains a dispersant that is at least one selected from the group consisting of sodium tartrate, sodium citrate, sodium silicate, tripotassium orthophosphate, sodium polyphosphate, sodium polymetaphosphate, sodium hexametaphosphate, and sodium pyrophosphate.

The filters preferably have a porosity of 4% to 90% and more preferably 15% to 90%.

Fine precipitates and the like (particularly a size of 1 µm or less and more preferably 200 nm or less) can be separated without being lost or aggregated and therefore the precipitates and the like can be accurately analyzed by size. Results obtained by our analytical method lead to new findings on properties of metal materials and provide suggestions useful in finding the cause of product failure or useful in developing novel materials.

Our analytical method is characterized in that precipitates and the like attached to a metal sample are separated without being aggregated by immersing a remaining portion of the electrolyzed metal sample having precipitates and the like attached thereto in a dispersible solution and the precipitates and the like separated in the dispersible solution are fractionated with filters having straight pores and a porosity of 4% or more and are then analyzed. The following procedures are described below in detail using a steel sample as an example: a procedure for optimizing the dispersible solution, which is used to separate the precipitates and the like, and a procedure for fractionating and analyzing the separated precipitates and the like.

(1) Procedure for Optimizing Dispersible Solution

Figure 2:
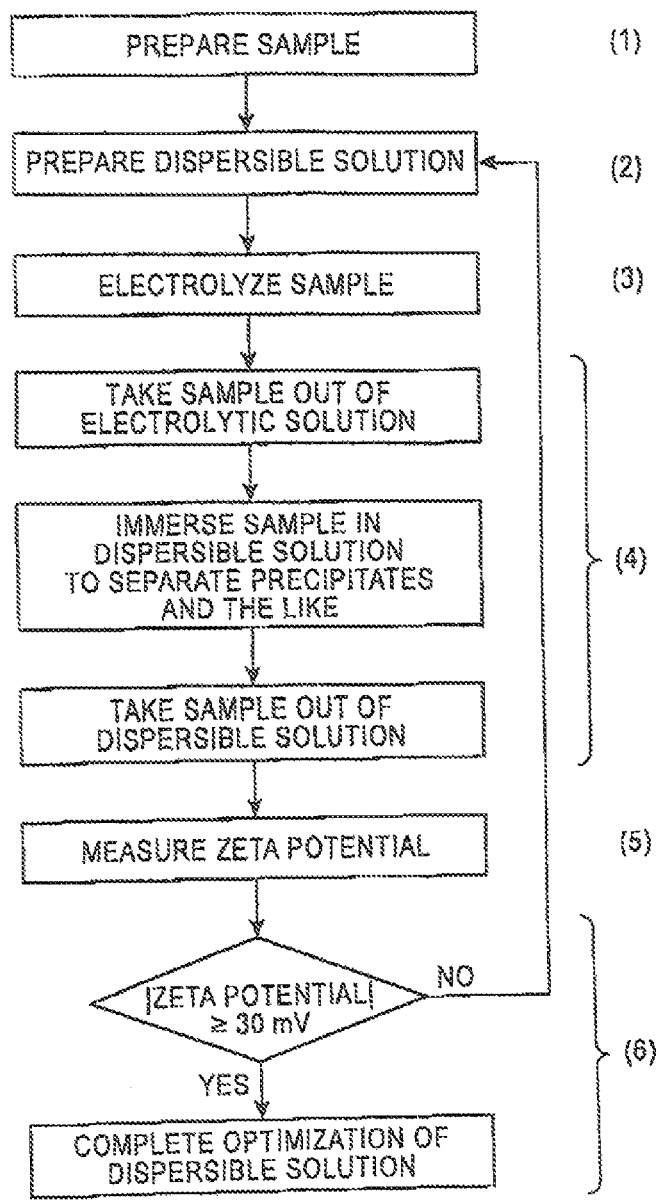
FIG. 2 is an illustration showing an example of an operational flow for optimizing a dispersible solution.

FIG. 2 shows an operational flow for optimizing the dispersible solution. The dispersible solution is optimized in accordance with Steps (1) to (6) shown in FIG. 2. Each step is performed as described below in detail.

Step (1): A steel material is machined into an electrolytic sample with an appropriate size.

Step (2): The dispersible solution, which is used to separate the precipitates and the like, is prepared separately from an electrolytic solution that is different from the dispersible solution. The amount of the dispersible solution that is half the amount of electrolytic solution is sufficient to disperse the precipitates and the like attached to the electrolytic sample in the dispersible solution. A dispersant contained in the dispersible solution is described below.

Step (3): A predetermined amount of the sample is electrolyzed. The term "predetermined amount" as used herein refer to the amount appropriately set and also refers to the amount sufficient to measure the zeta potential described below or sufficient to analyze elements. Electrolysis can be performed using an electrolyzer 7 shown in FIG. 3. The electrolyzer 7 includes a fixture 2 for fixing a sample 1, an electrode 3, an electrolytic solution 6, a beaker 4 for storing the electrolytic solution 6, and a constant-current power supply 5 for supplying a current. The fixture 2 is connected to the anode of the constant-current power supply 5 and the electrode 3 is connected to the cathode of the constant-current power supply 5. The sample 1 is connected to the fixture 2 and is immersed in the electrolytic solution 6. The electrode 3 is immersed in the electrolytic solution 6 and is placed so as to cover the surface of the sample 1 immersed in the electrolytic solution 6. When the sample is an ordinary steel material, it is most easy to use a permanent magnet as the fixture 2. Since the permanent magnet may possibly be dissolved by contact with the electrolytic solution 6, a platinum plate is used for a portion likely to be in contact with the electrolytic solution 6, that is, a portion 2a shown in FIG. 3. Likewise a platinum plate is used to prevent the electrode 3 from being dissolved by the electrolytic solution 6. The sample 1 is electrolyzed by supplying a charge from the constant-current power supply 5 to the electrode 3. The amount of the electrolyzed sample is proportional to the coulomb and therefore depends on the time of electrolysis when a current is constant.

Step (4): The sample that remains without being electrolyzed is taken out of the electrolytic solution and is then immersed in the dispersible solution prepared in Step (2), whereby the precipitates and the like attached to the sample are separated in the dispersible solution. In this operation, to efficiently strip the precipitates and the like from the sample to separate the precipitates and the like in the dispersible solution, ultrasonic waves are preferably applied to the sample in such a state that the sample is immersed in the dispersible solution. The sample is then taken out of the dispersible solution. When being taken out thereof, the sample is preferably washed with the same solution as the dispersible solution.

Step (5): The dispersible solution separated from the precipitates and the like is measured for zeta potential after Step (4).

Step (6): When the absolute value of the zeta potential determined in Step (5) is less than 30 mV, the type and/or concentration of the dispersant is changed and Steps (2) to (6) are repeated. In contrast, when the absolute value of the zeta potential is 30 mV or more, the dispersible solution is regarded as being optimized.

In FIG. 2, the dispersant and the concentration thereof are determined to be optimum conditions of the dispersible solution for the precipitates and the like when the measured zeta potential is 30 mV or more. There is no problem as long as the precipitates and the like are not aggregated but are sufficiently dispersed in the dispersible solution. Hence, an indicator of the optimization of the dispersible solution is not limited to the zeta potential. The relationship between the dispersible solution and the zeta potential is described below in detail.

(2) Procedure for Fractionating and Analyzing Precipitates and the Like

Figure 4:
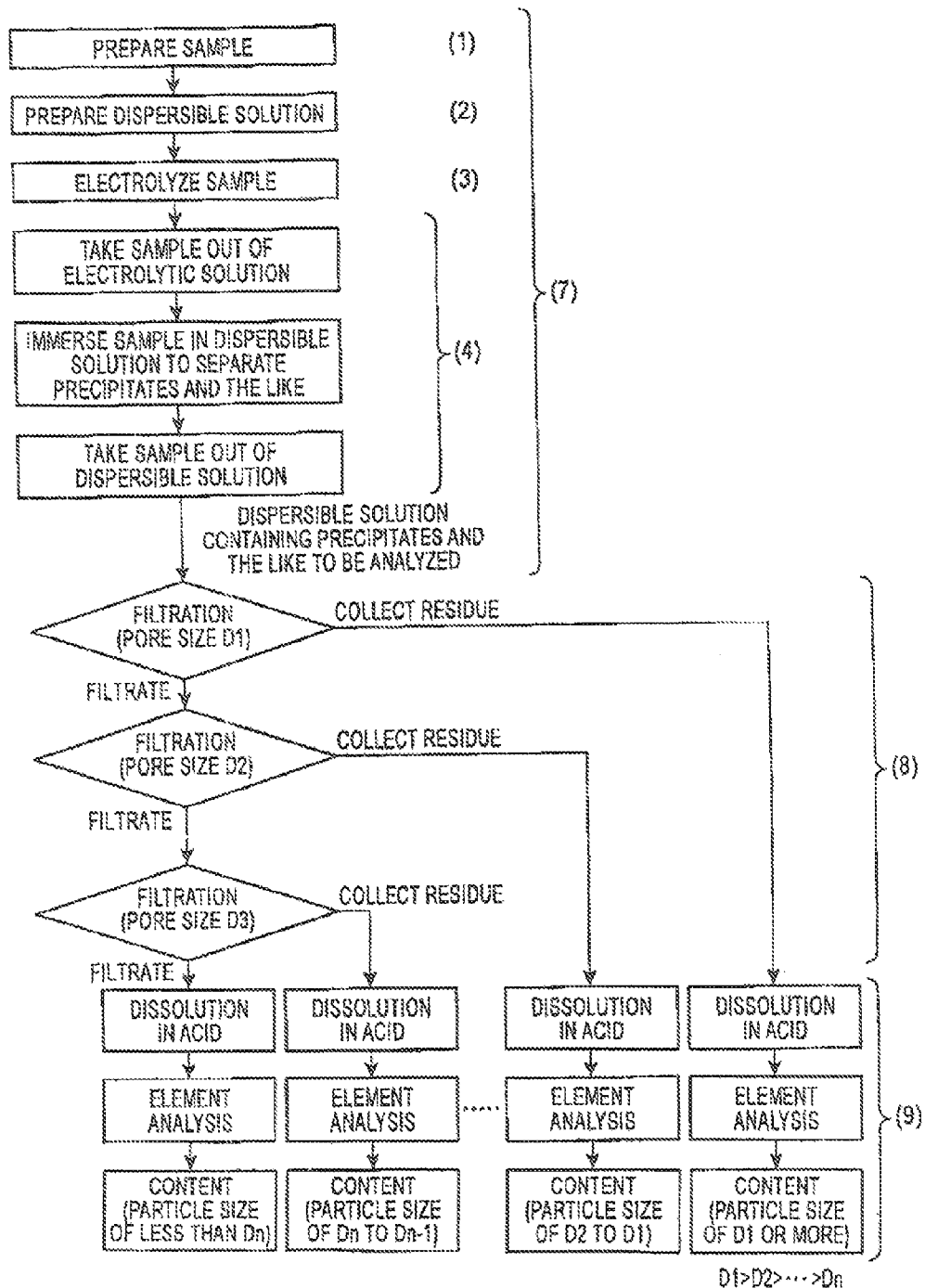

FIG. 4 shows an operational flow for fractionating the precipitates and the like separated in the dispersible solution by size and analyzing the precipitates and the like. The precipitates and the like are fractionated and analyzed in accordance with Steps (7) to (9) shown in FIG. 4. Each step is performed as described below in detail.

Step (7): The dispersible solution optimized by an operation shown in FIG. 2 is used and the precipitates and the like are separated in the dispersible solution in accordance with Steps (1) to (4) similar to those shown in FIG. 2.

Step (8): The dispersible solution containing the precipitates and the like are filtered through a filter having straight pores and a porosity of 4% or more and a residue trapped on the filter and a filtrate are collected. In the case of fractionating the precipitates and the like into (n+1) fractions by size, n filters having different filter pore sizes are prepared, the dispersible solution is filtered through the filters in decreasing order of filter pore size n times, and the residue trapped on the filter each time and the nth filtrate are collected.

Step (9): The residues, which are trapped on the filters, and filtrates obtained by the operation of Step (8) are each dissolved in an acid and are then subjected to elemental analysis, whereby the content of an element contained in the precipitates and the like fractionated by size is determined. In this case, all the residues and filtrates obtained above need not be subjected to elemental analysis and only a residue corresponding to a necessary size may be analyzed. In the case of performing filtration several times, the finally obtained filtrate (which can be expected to contain the finest precipitates and the like) only may be analyzed or only a single residue obtained in an intermediate stage may be analyzed.

The above-mentioned analytical method can be used to analyze precipitates and the like contained in various metal materials, is particularly suitable for steel materials containing precipitates and the like with a size of 1 μm or less, and is more suitable for steel materials containing precipitates and the like with a size of 200 nm or less.

(3) Dispersible Solution

The dispersible solution prepared in Step (2) is supplemented below. There are no useful dispersible solutions capable of separating precipitates and the like with a size of 1 μm or less without aggregating the precipitates and the like at present. Therefore, aqueous solutions of dispersants used for particles with a size of 1 μm or more have been investigated, resulting in that there are no clear correlations between the types and concentrations of the dispersants, the composition of and sizes of precipitates and the like, and the densities of the precipitates and the like in the solutions. Preferred examples of the dispersants include sodium tartrate, sodium citrate, sodium silicate, tripotassium orthophosphate, sodium polyphosphate, sodium polymeta-phosphate, sodium hexametaphosphate, and sodium pyrophosphate. It has been found that when the concentration of each dispersant is greater than an appropriate level, the precipitates and the like are aggregated.

Thus, in the optimization of the dispersible solution, the type and/or concentration of the dispersant is accordingly optimized depending on the density or properties the precipitates and the like or a subsequent analytical technique.

The reason for using the zeta potential as an indicator of the optimization of the dispersible solution is that there is a close correlation between the surface charge and the dispersibility of precipitates and the like in the case of using an aqueous solution containing the dispersant and therefore optimum conditions (the type, appropriate concentration, and so on of the dispersant) of the dispersible solution can be fixed by identifying the surface charge condition of the precipitates and the like using a zeta potentiometer. That is, since smaller precipitates and the like are more likely to be aggregated in liquids, the use of an appropriate dispersant at an appropriate concentration allows charges to be imparted to surfaces of precipitates and the like and therefore the precipitates and the like repel each other and are probably prevented from being aggregated.

This result suggests that the use of the zeta potential as an indicator for the purpose of determining the type and concentration of the dispersible solution is a simple way and is preferred in that optimum conditions (the type, appropriate concentration, and so on of the dispersant) of the dispersible solution can be fixed. We found that the absolute value of the zeta potential is preferably large to disperse precipitates and the like. Furthermore, we found that aggregation can be prevented and accurate analysis can be performed when the absolute value thereof is about 30 mV or more.

Thus, the value of the zeta potential is preferably used as an indicator for the purpose of determining the type and concentration of the dispersible solution used to separate precipitates and the like and the dispersible solution preferably has a zeta potential with an absolute value of 30 mV or more with respect to the precipitates and the like.

(4) Filters

The filters used in Step (8) are supplemented below. Since our method is central to fractionating precipitates and the like by size, precipitates and the like larger than filter pore sizes and precipitates and the like smaller than filter pore sizes need to be securely fractionated. Therefore, the filters need to have a porosity of 4% or more and the straight pores as described above. When the porosity thereof is less than 4%, pores thereof are seriously clogged with coarse particles or aggregated particles, which is unsuitable. The porosity thereof is preferably large. The porosity thereof is preferably 15% or more and more preferably 45% or more. However, it is not sufficient that the porosity thereof is large. It is a sufficient condition that the filters have the straight pores in addition to a porosity of 4% or more and the straight pores have substantially a uniform size and extend substantially straight from the front surface to the rear surface of each filter.

Filters nonuniform in pore size have a low capability to separate precipitates and the like by size and therefore is not suitable. To exert advantageous effects, the filters preferably have a large porosity. However, for the straight pores, it is difficult to increase the porosity thereof to greater than about 90%. This is because when equal-sized circles (pores) are arranged in a plane, the percentage of the pores in the plane is up to slightly over 90%. Thus, the porosity of the filters is preferably 90% or less in consideration of the strength of the filters. An example of the calculation of the porosity thereof is the following equation (1):

$$\text{porosity} = (\text{filter volume} - \text{filter weight/density})/\text{filter volume} \times 100 \, (\%) \quad (1).$$

Example 1

The relationship between the content of titanium in precipitates and the like and the zeta potential in accordance with Steps (1) to (6) shown in FIG. 2. Detailed conditions of each operation are as described below. Our method is not limited to the detailed conditions.

Figure 3:
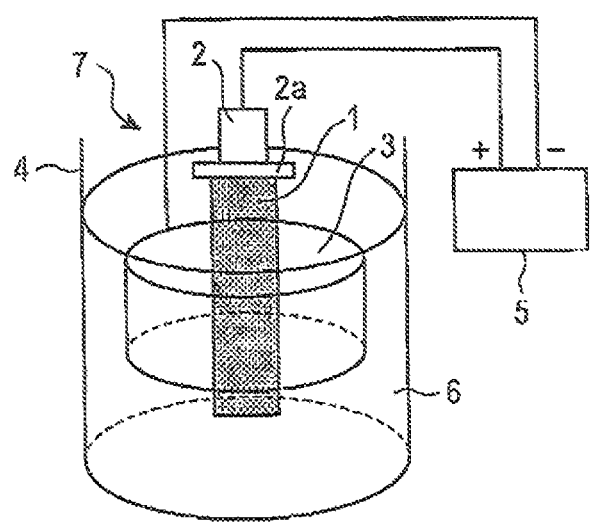
Figure 5:
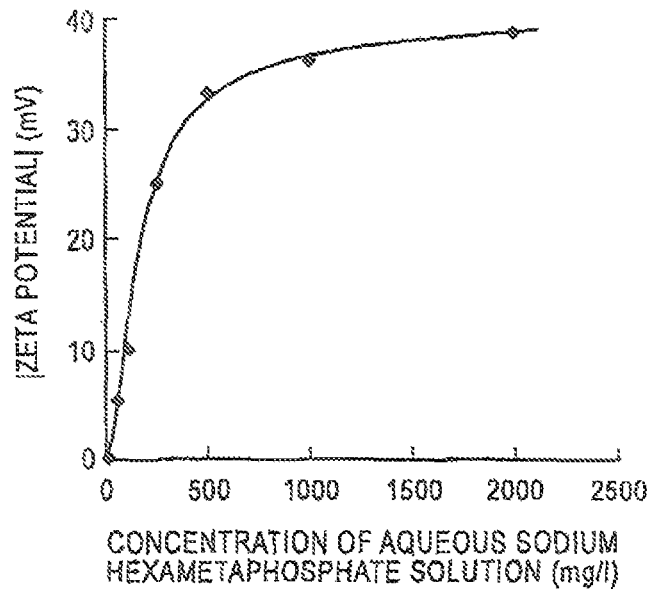
FIG. 5 is a graph showing the relationship between the concentration of an aqueous solution of sodium hexametaphosphate and the absolute value of the zeta potential.

Titanium-added carbon steel containing 0.09% C, 0.12% Si, 1.00% Mn, 0.010% P, 0.003% S, 0.18% Ti, and 0.0039% N on a mass basis was electrolyzed in about 300 ml of a 10% AA electrolytic solution (10% by volume of acetylacetone-1% by mass of tetramethylammonium chloride-methanol) using an electrolyzer shown in FIG. 3. After electrolysis, portions of the remaining carbon steel were immersed in seven aqueous solutions of sodium hexametaphosphate (hereinafter referred to as SHMP) with a concentration ranging from 0 mg/l to 2000 mg/l, the aqueous solutions being dispersible solutions, precipitates and the like were separated therein, and the zeta potential was measured with a zeta potentiometer at each concentration. The results show that the absolute value of the zeta potential increases with an increase in SHMP concentration as shown in FIG. 5. Results similar to those shown in FIG. 5 were obtained using aqueous sodium pyrophosphate solutions. This shows that the zeta potential can be controlled by the type and/or concentration of a dispersant.

Figure 6:
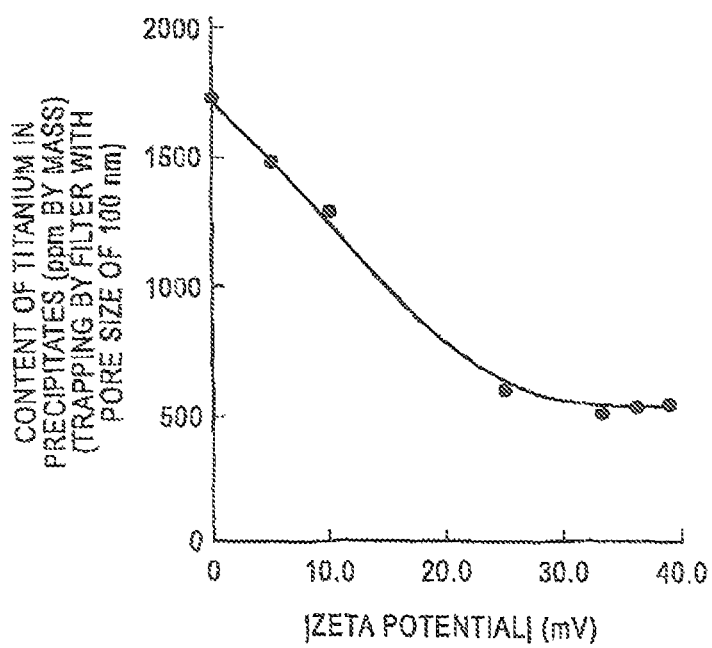

Operations of Steps (7) to (9) shown in FIG. 4 were performed using a filter having straight pores, a porosity of 47% as determined by microscopy, and a filter pore size of 100 nm, whereby the content of titanium (the percentage of titanium in steel) in precipitates and the like with a size of 100 nm or more was determined (in Example 1, the size of precipitates and the like which did not pass through the filter and which were trapped on the filter was defined as 100 nm or more). As shown in FIG. 6, the results show that when the absolute value of the zeta potential is less than 30 mV, a reduction in zeta potential causes the aggregation of the precipitates and the like and increases the apparent content of titanium in the precipitates and the like and also show that when the absolute value of the zeta potential is 30 mV or more, the content of titanium in the precipitates is constant and the dispersion of the precipitates and the like is good.

In our analytical method, there is no problem if precipitates and the like are not aggregated but are sufficiently dispersed in a dispersible solution. Hence, an indicator of the optimization of the dispersible solution is not limited to the zeta potential.

Example 2

An example of analysis using colloidal gold particles with a known size is herein described in detail.

A predetermined amount of each of six different types of commercially available colloidal gold solutions with a particle size of 20, 30, 40, 50, 60, or 80 nm was filtered through three types of Filters A, B, and C shown in Table 1. After obtained filtrates were dried, obtained residues were heated, were dissolved in aqua regia, and were then measured for gold concentration with an ICP mass spectrometer, whereby the amount of colloidal gold in each of the colloidal gold solutions passing through the filters was determined. Furthermore, 5 ml of each colloidal gold solution was dried without being filtered and was measured for gold concentration in the same manner as above, whereby the standard amount of colloidal gold in the colloidal gold solution was determined. The amount of colloidal gold in each of the colloidal gold solutions passing through the filters was divided by the standard amount of colloidal gold in a corresponding one of the colloidal gold solutions, whereby the filter penetration thereof was calculated. For filter porosities shown in Table 1, the porosity of Filter A and that of Filter B were determined by electron microscopy and the porosity of Filter C was quoted from a catalogue.

Figure 7:
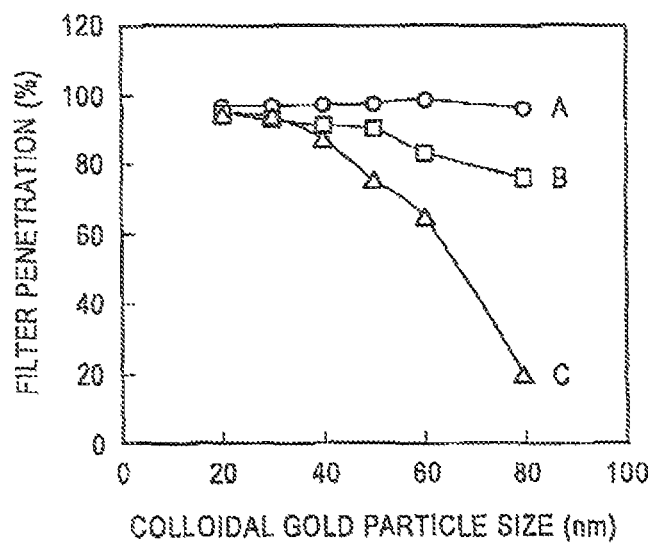
FIG. 7 is a graph showing the relationship between the size of colloidal gold particles used in Example 2 and the filter penetration thereof.

FIG. 7 shows the relationship between the size of colloidal gold particles and the filter penetration thereof. The colloidal gold particles with a size of 40 nm or less exhibit good filter penetration for every filter. However, the colloidal gold particles with a size of greater than 40 nm vary in filter penetration depending on the filters. That is, for Filter A, which has straight pores and a porosity of 47%, a filter penetration of about 100% is achieved independently of the colloidal gold particle size. For Filter B, which has straight pores and a small porosity of 4%, a high filter penetration of 80% or more is achieved although the filter penetration decreases with an increase in colloidal gold particle size. Meanwhile, for Filter C, which has non-straight pores different from straight pores and a large porosity of 70%, the filter penetration decreases significantly with an increase in colloidal gold particle size. Filter B has low porosity and therefore the physical interface between the particles probably causes the clogging of the filter pores to cause a slight reduction in filter penetration. The occurrence of such clogging has no influence on the analysis accuracy of actual precipitates and the like. Filter C has high porosity and, however, has the non-straight pores. Hence, the pore size distribution thereof is wide and the fractionation capability thereof by size is significantly low. This causes a reduction in the analysis accuracy of actual precipitates and the like.

TABLE 1

| Filters | Filter pore size (mm) | Porosity (%) | Pore shape |
|---|---|---|---|
| A | 100 | 47 | Straight |
| B | 100 | 4 | Straight |
| C | 100 | 70 | Non-straight |

When the porosity is less than 4%, filter pores are seriously clogged with coarse precipitates and the like or aggregates of precipitates and the like. The porosity is preferably high and particularly preferably 45% or more.

Example 3

Another example of analysis using colloidal gold particles with a known size is herein described in detail.

A predetermined amount of each of eight different types of commercially available colloidal gold solutions with a particle size of 20, 30, 40, 50, 60, 80, 100, or 150 nm was filtered through three types of Filters D, E, and F shown in Table 2. After obtained filtrates were dried, residues thereby obtained were heated, were dissolved in aqua regia, and were then measured for gold concentration with an ICP mass spectrometer, whereby the amount of colloidal gold in each of the colloidal gold solutions passing through the filters was determined. Furthermore, 5 ml of each colloidal gold solution was dried without being filtered and measured for gold concentration in the same manner as above, whereby the standard amount of colloidal gold in the colloidal gold solution was determined. The amount of colloidal gold in each of the colloidal gold solutions passing through the filters was divided by the standard amount of colloidal gold in a corresponding one of the colloidal gold solutions, whereby the filter penetration thereof was calculated. For filter porosities shown in Table 2, the porosity of Filter D and that of Filter E were determined by electron microscopy and the porosity of Filter F was quoted from a catalogue.

Figure 8:
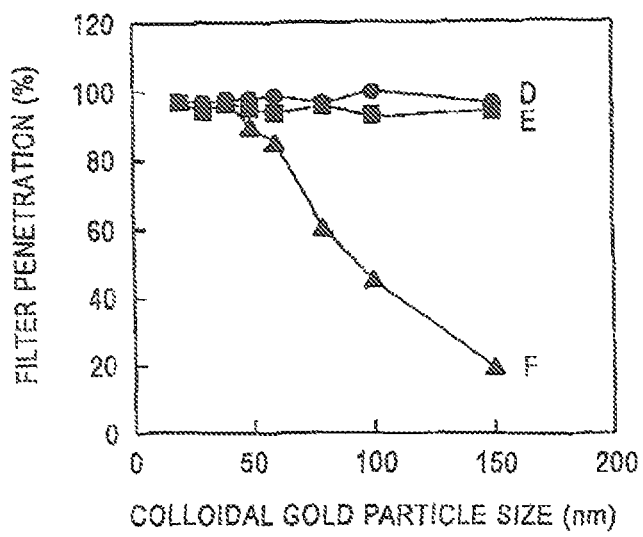
FIG. 8 is a graph showing the relationship between the size of colloidal gold particles used in Example 3 and the filter penetration thereof.

FIG. 8 shows the relationship between the size of colloidal gold particles and the filter penetration thereof. The colloidal gold particles with a size of 60 nm or less exhibit good filter penetration for every filter. However, the colloidal gold particles with a size of greater than 60 nm vary in filter penetration depending on the filters. That is, for Filter D, which has straight pores and a porosity of 50%, a filter penetration of about 100% is achieved independently of the colloidal gold particle size. For Filter E, which has straight pores and a slightly small porosity of 15%, a high filter penetration of 90% or more is achieved although the filter penetration decreases with an increase in colloidal gold particle size. Meanwhile, for Filter F, which has non-straight pores different from straight pores and a large porosity of 75%, the filter penetration decreases significantly with an increase in colloidal gold particle size. Filter F, as well as Filter B, has low porosity and therefore the physical interface between the particles probably causes the clogging of the filter pores to cause a slight reduction in filter penetration. The occurrence of such clogging has no influence on the analysis accuracy of actual precipitates and the like. Filter F, as well as Filter C, has high porosity and, however, has the non-straight pores. Hence, the pore size distribution thereof is wide and the fractionation capability thereof by size is significantly low. This leads to a reduction in the analysis accuracy of actual precipitates and the like.

TABLE 2

| Filters | Filter pore size (mm) | Porosity (%) | Pore shape |
|---|---|---|---|
| D | 200 | 50 | Straight |
| E | 200 | 15 | Straight |
| F | 200 | 75 | Non-straight |

The results of Examples 2 and 3 show that a filter for fractionating precipitates and the like by size needs to have straight pores and also needs to have a porosity of 4% or more, more preferably 15% or more, and further more preferably 45% or more.

Example 4

In this example, the following cases are described in detail: the cases where precipitates and the like separated from steel were filtered and were then analyzed by an analytical method, using straight-pore filters (a porosity of 47% or 4%), our method (Example); the precipitates and the like were filtered and were then analyzed by an analytical method using non-straight-pore filters instead of such straight-pore filters (Comparative Example 1); the precipitates and the like were filtered and were then analyzed by a method disclosed in JP '383 (Comparative Example 2); and the precipitates and the like were filtered and were then analyzed by a method disclosed in The Iron and Steel Institute of Japan, "Handbook of Iron and Steel 4th edition (CD-RM)," Vol. 4, Section 2, 3.5 (Comparative Example 3).

Example

About 0.5 g of each of Samples 1 to 4, cut out from carbon steels containing components shown in Table 3, having a size of 20 mm×50 mm×1 mm was galvanostatically electrolyzed at a current density of 20 mA/cm$^2$ in about 300 ml of a 10% AA electrolytic solution using an electrolyzer shown in FIG. 3. Thereafter, each sample was gently taken out of the electrolytic solution and was then immersed in about 100 ml of an aqueous SHMP solution, prepared in a separate vessel, having a concentration of 500 mg/l, the aqueous SHMP solution being a dispersible solution. Precipitates and the like attached to the sample were stripped off in the vessel by ultrasonic vibration, whereby the precipitates and the like were separated in the aqueous SHMP solution. After the sample exhibited a metallic luster, ultrasonic vibration was stopped. The sample was taken out of the vessel, was washed with the aqueous SHMP solution and pure water, and was then dried. The sample was weighed with a balance. The weight of the electrolyzed sample was subtracted from the weight of the unelectrolyzed sample, whereby the electrolysis weight was determined.

The following solutions were filtered in a suction filtration apparatus equipped with Filter A shown in Table 1 in this order: the aqueous SHMP solution separated from the precipitates and the like attached to the sample and a colloidal gold-containing aqueous SHMP solution prepared by adding 1 ml of a colloidal gold solution with a particle size of 60 nm to 50 ml of a aqueous SHMP solution with a concentration of 500 mg/l. After the filter and a residue trapped on the filter were heated and dissolved in a mixture of nitric acid, perchloric acid, and sulfuric acid, an obtained solution was analyzed with an ICP emission spectrometer, whereby the absolute amount of titanium in the residue was determined. The absolute amount of titanium in the residue was divided by the electrolysis weight, whereby the content of titanium in the precipitates and the like that did not pass through Filter A was determined. A filtrate passing through Filter A was dried by heating the filtrate on an 80° C. hotplate. After a dry residue remaining after drying was heated and dissolved in a mixture of nitric acid, perchloric acid, and sulfuric acid, the absolute amount of titanium and that of gold in the filtrate were measured with an ICP emission spectrometer or an ICP mass spectrometer. The absolute amount of titanium in the filtrate was divided by the electrolysis weight, whereby the content of titanium in the precipitates and the like that passed through Filter A was determined. Likewise, the absolute amount of gold therein was divided by the standard amount of gold, whereby the filter penetration of colloidal gold through Filter A was determined. The term "the standard amount of gold" as used herein refers to the absolute amount of gold that is determined in such a manner that the colloidal gold-containing aqueous SHMP solution unfiltered through Filter A is dried and is then decomposed with aqua regia and the decomposed matter is measured with an ICP mass spectrometer.

Similar operations were performed using Filter B shown in Table 1, whereby the content of titanium in the precipitates and the like that did not pass through Filter B, the content of titanium in the precipitates and the like that passed through Filter B, and the filter penetration of colloidal gold through Filter B were determined.

Comparative Example 1

Substantially the same operations as those described in the Example were performed except that Filter C shown in Table 1 was used, whereby the content of titanium in the precipitates and the like that did not pass through Filter C, the content of titanium in the precipitates and the like that passed through Filter C, and the filter penetration of colloidal gold through Filter C were determined.

Comparative Example 2

Substantially the same operations as those described in the Example were performed except that methanol was used as a dispersible solution for separating the precipitates and the like attached to each sample instead of the aqueous SHMP solution and Filter C shown in Table 1 was used, whereby the content of titanium in the precipitates and the like that did not pass through Filter C, the content of titanium in the precipitates and the like that passed through Filter C, and the filter penetration of colloidal gold through Filter C were determined. Incidentally, the colloidal gold-containing aqueous SHMP solution was used to determine the filter penetration of colloidal gold in substantially the same manner as that described in the Example.

Comparative Example 3

Substantially the same operations as those described in Comparative Example 2 were performed except that Filter B shown in Table 1 was used instead of Filter C, whereby the content of titanium in the precipitates and the like that did not pass through Filter B, the content of titanium in the precipitates and the like that passed through Filter B, and the filter penetration of colloidal gold through Filter B were determined.

Figure 9:
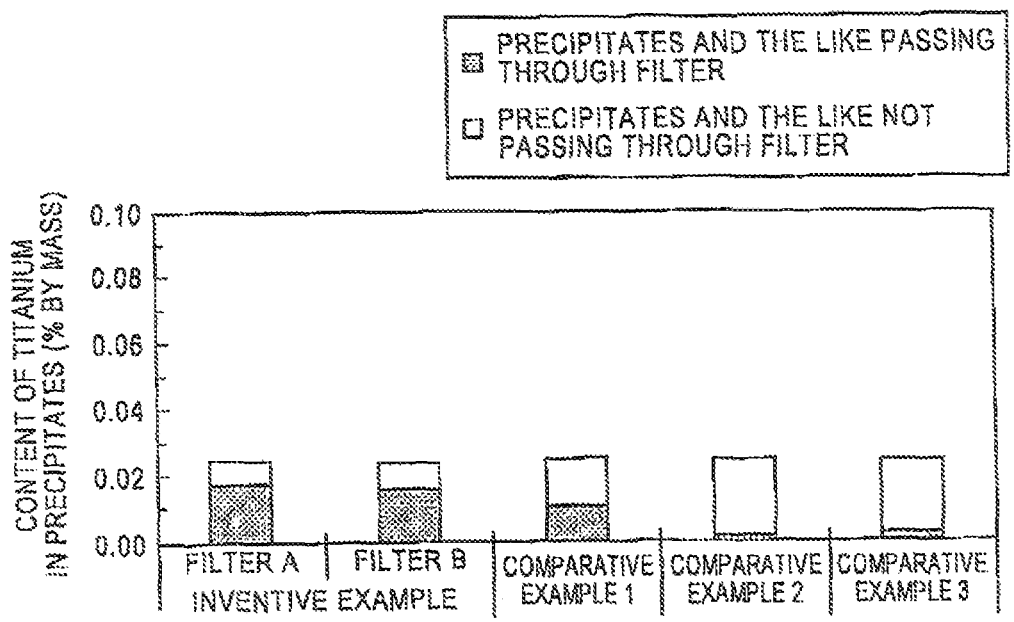
FIG. 9 is a graph showing the content of titanium in precipitates and the like contained in Sample 1 used in Example and Comparative Examples.
Figure 10:
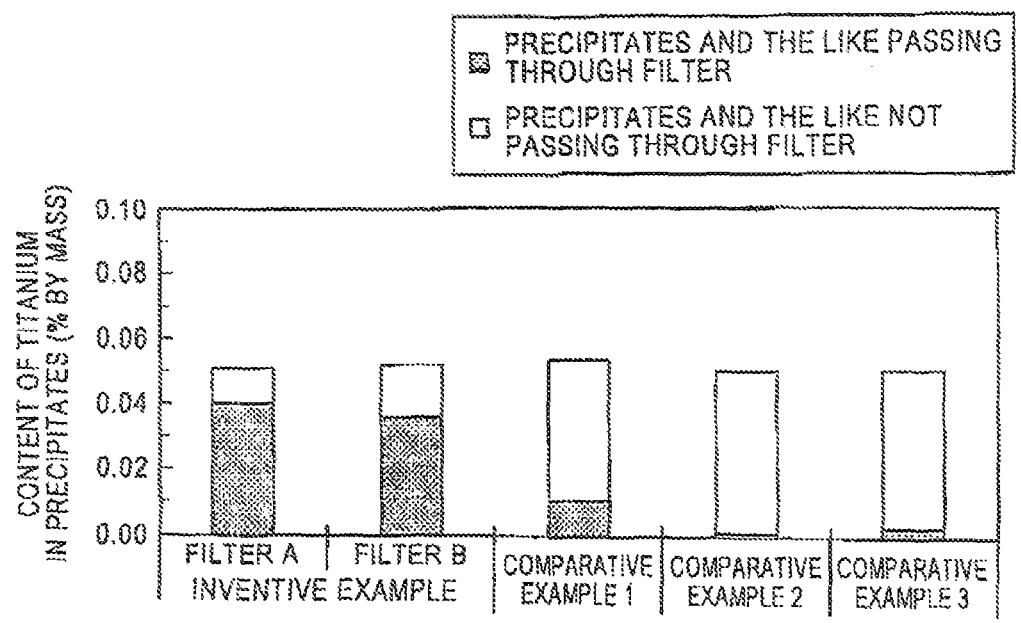
FIG. 10 is a graph showing the content of titanium in precipitates and the like contained in Sample 2 used in Example and Comparative Examples.
Figure 11:
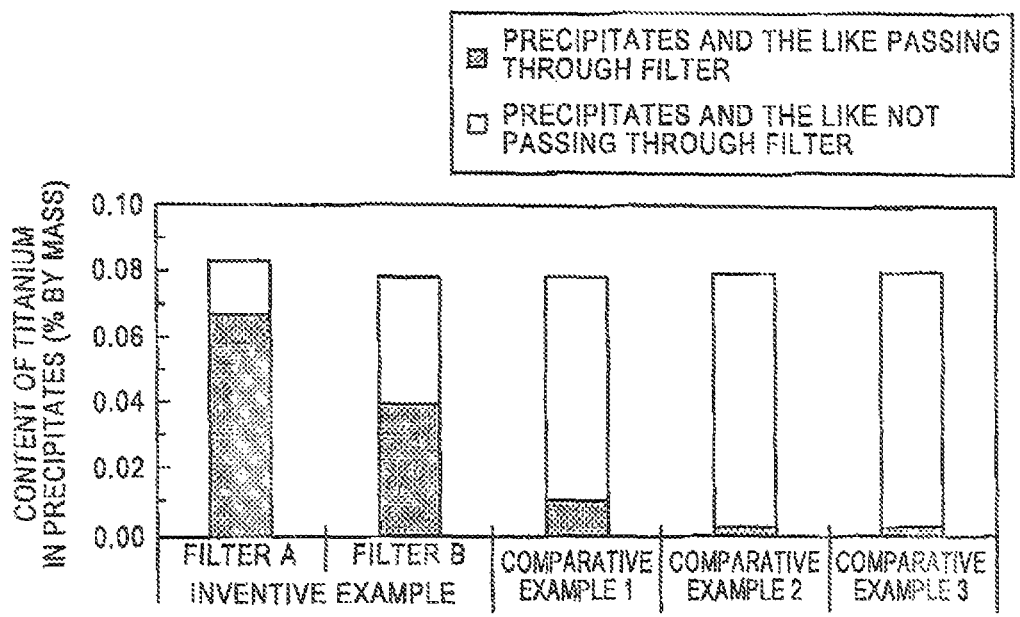
FIG. 11 is a graph showing the content of titanium in precipitates and the like contained in Sample 3 used in Example and Comparative Examples.
Figure 12:
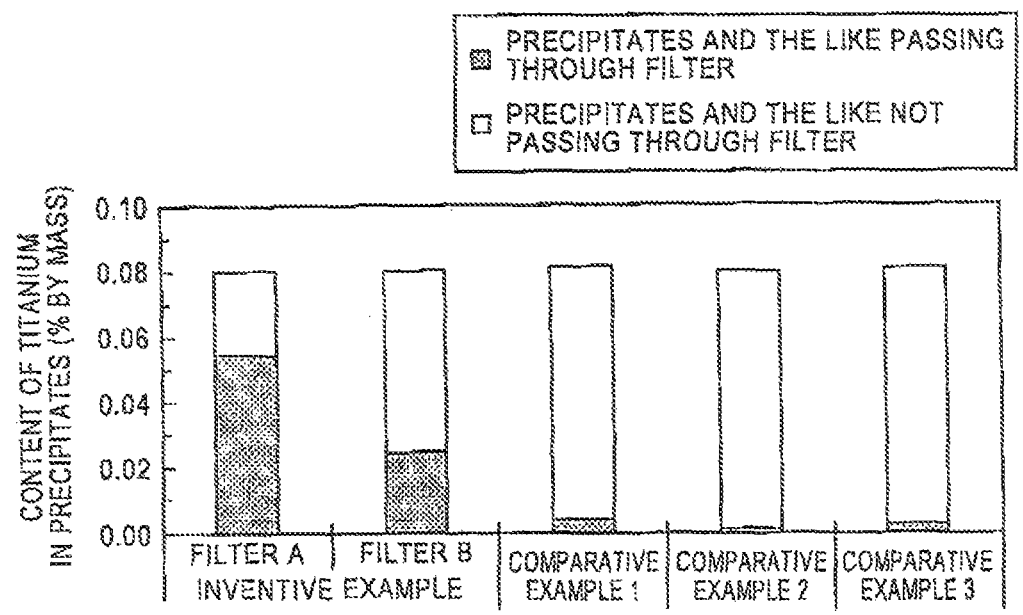
FIG. 12 is a graph showing the content of titanium in precipitates and the like contained in Sample 4 used in Example and Comparative Examples.
Figure 13:
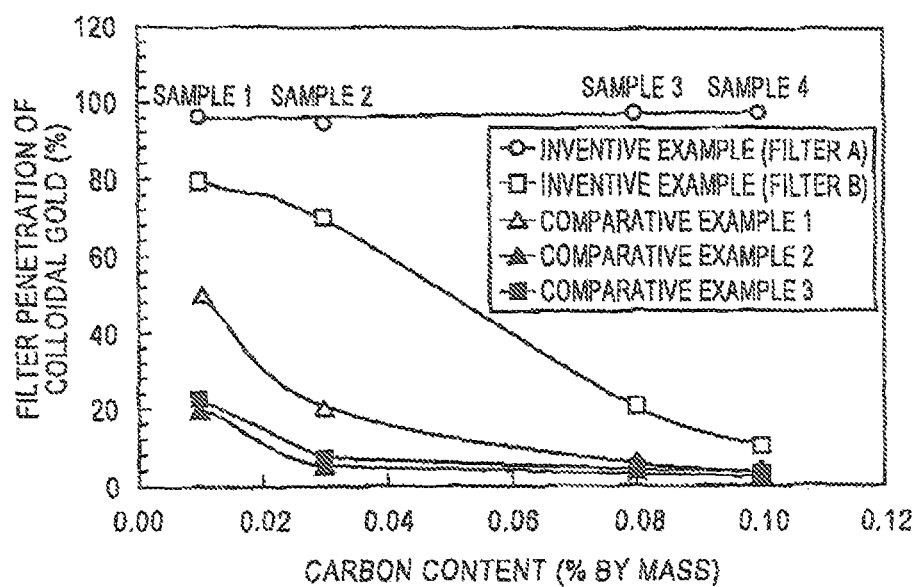
FIG. 13 is a graph showing the relationship between the carbon content of steel and the filter penetration of colloidal gold.

FIG. 9 shows results of Sample 1, FIG. 10 shows results of Sample 2, FIG. 11 shows results of Sample 3, and FIG. 12 shows results of Sample 4. FIG. 13 shows the relationship between the carbon content of steel and the filter penetration of colloidal gold.

The amount of Ti-containing precipitates and the like in steel correlates with the carbon content thereof. Therefore, in the case of the same production conditions except components, it can be regarded that the amount of the precipitates and the like in the Sample 4 is largest and the amount of the precipitates and the like decreases in this order: Sample 3, Sample 2, and Sample 1. That is, when Ti-containing precipitates and the like in Sample 4 are analyzed, a cake layer is most likely to be formed. In contrast, Sample 1 is least. The formation of cake layers causes differences between results obtained by fractionating precipitates and the like by size and probably affects the filter penetration of colloidal gold filtered subsequently. In consideration of these points, the results are explained below.

FIGS. 9 to 12 illustrate that in every sample, the content of titanium in fine precipitates and the like passing through a filter used in the Example is greater than that in an comparative example and this tendency is remarkable in Sample 3 (FIG. 11) and Sample 4 (FIG. 12), which contain a large amount of precipitates and the like and have a high carbon content. In particular, for Sample 4, precipitates and the like passing through a filter are hardly detected in Comparative Examples 1 to 3. Results of Comparative Examples 1 to 3 suggest that, in every sample, precipitates and the like were aggregated and were not securely fractionated by the formation of cake layers, because the filter penetration of colloidal gold is low as shown in FIG. 13. Accordingly, the content of titanium in the precipitates and the like determined in each of Comparative Examples 1 to 3 cannot be regarded as a correct value.

In the Example using Filter A, since the filter penetration of colloidal gold in every sample is as high as 90% or more as shown in FIG. 13, precipitates and the like were probably appropriately fractionated by size without the formation of a cake layer. Accordingly, the content of titanium in the precipitates and the like determined in the Example using Filter A can be regarded as a correct value. In the Example using Filter B, the filter penetration of colloidal gold in each of Samples 3 and 4 is low and that in each of Samples 1 and 2 is, however, high as shown in FIG. 13. Hence, for Samples 1 and 2, which have a low carbon content and contain a small amount of precipitates and the like, the precipitates and the like were appropriately fractionated by size without the formation of a cake layer and therefore the content of titanium in the precipitates and the like can be regarded as a correct value. For Samples 3 and 4, of which the filter penetration is low but not zero, the content of titanium in the precipitates and the like can be regarded as a correct value, which is slightly low in accuracy.

TABLE 3

| Samples | C | Si | Mn | Ti | N |
|---|---|---|---|---|---|
| 1 | 0.01 | 0.1 | 1.0 | 0.08 | 0.0020 |
| 2 | 0.03 | 0.1 | 1.0 | 0.08 | 0.0020 |
| 3 | 0.08 | 0.1 | 1.0 | 0.08 | 0.0020 |
| 4 | 0.10 | 0.1 | 1.0 | 0.08 | 0.0020 |

The invention claimed is:

1. A method for analyzing Ti in precipitates and inclusions including a Ti compound in a Ti-containing steel material, comprising:

an electrolysis step of partially electrolyzing a Ti-containing steel sample in an electrolytic solution, whereby precipitates and inclusions including a Ti compound attach to a remaining portion of the steel sample;

an immersion step of immersing a remaining portion of the steel sample taken out of the electrolytic solution with the precipitates and inclusions attached thereto in a dispersing solution;

a fractionation step of filtering precipitates and/or inclusions including a Ti compound separated in the dispersing solution using filters having straight pores and a porosity of 4% or more once or more, wherein the straight pores extend through the filters; and an analysis step of analyzing one or more of the precipitates and the inclusions trapped on one or more of the filters and the precipitates and the inclusions passing through one or more of the filters.

2. The method according to claim 1, wherein in the analysis step, the precipitates and the inclusions having a size of less than 1 μm are analyzed.

3. The method according to claim 1, wherein in the analysis step, the precipitates and the inclusions attached to the remaining portion of the steel sample are analyzed.

4. The method according to claim 2, wherein in the analysis step, the precipitates and the inclusions attached to the remaining portion of the steel sample are analyzed.

5. The method according to claim 1, wherein the dispersing solution has a zeta potential with an absolute value of 30 mV or more with respect to the precipitates and the inclusions to be analyzed.

6. The method according to claim 2, wherein the dispersing solution has a zeta potential with an absolute value of 30 mV or more with respect to the precipitates and the inclusions to be analyzed.

7. The method according to claim 3, wherein the dispersing solution has a zeta potential with an absolute value of 30 mV or more with respect to the precipitates and the inclusions to be analyzed.

8. The method according to claim 4, wherein the dispersing solution has a zeta potential with an absolute value of 30 mV or more with respect to the precipitates and the inclusions to be analyzed.

* * * * *